USOO5649965A

United States Patent [19]
Pons et al.

[11] Patent Number: 5,649,965
[45] Date of Patent: Jul. 22, 1997

[54] PROTECTION AGAINST ELECTROMAGNETIC PERTURBATIONS OF EXTERNAL ORIGIN FOR A ACTIVE IMPLANTABLE DEVICE

[75] Inventors: Pascal Pons, Crolles; Renzo Dal Molin, Chatillon, both of France

[73] Assignee: Ela Medical S.A., Montrouge, France

[21] Appl. No.: 577,227

[22] Filed: Dec. 22, 1995

[30] Foreign Application Priority Data

Dec. 30, 1994 [FR] France ................... 94 15911

[51] Int. Cl.$^6$ ............................................ A61N 1/37
[52] U.S. Cl. ................................. 607/2; 607/63
[58] Field of Search .................... 607/2, 4, 7, 9, 607/11, 34, 63, 5; 128/901, 908; 323/901, 908

[56] References Cited

U.S. PATENT DOCUMENTS

| | | | |
|---|---|---|---|
| 4,363,324 | 12/1982 | Kusserow | 607/63 |
| 4,379,459 | 4/1983 | Stein | 607/9 |
| 4,739,437 | 4/1988 | Morgan | 361/88 |
| 4,745,923 | 5/1988 | Winstrom | 607/9 |
| 5,170,806 | 12/1992 | Colen | 128/901 |

FOREIGN PATENT DOCUMENTS

0 228 539   7/1986   European Pat. Off. ......... A61N 1/37

Primary Examiner—William E. Kamm
Assistant Examiner—George R. Evanisko
Attorney, Agent, or Firm—Orrick, Herrington & Sutcliffe, LLP

[57] ABSTRACT

An active implantable medical device, particularly a cardiac pacemaker or defibrillator, having a protection circuit that is effective against electromagnetic perturbations of external origin. The active implantable device is characterized in that at least all active components of the protection circuit (58, 60, 94, 98) are integrated components in a monolithically integrated microchip (16) including a control signal and circuits to commute selectively signals collected by external electrodes to the device for processing. In particular, the commutation circuits comprise static switches (24, 24', 28, 28', 38, 38', 40, 40', 44, 44', 46, 46', 50, 50', 54), and the control signal is a control voltage (VSUB, VCC) that is greater than the voltage (VPILE) of the battery of the device. The device delivers control logic signals (VDD, VSS) that are less than the battery voltage, and the protection circuit includes a voltage translator circuit (58) to raise, in absolute value, the logic control signal level to a value compatible with the static switches, control voltages and greater than the nominal level of parasitic voltages resulting from electromagnetic perturbations that are susceptible to appear on the static switch connection.

12 Claims, 4 Drawing Sheets

FIG_2

FIG_3

FIG_4

FIG_5

PROTECTION AGAINST ELECTROMAGNETIC PERTURBATIONS OF EXTERNAL ORIGIN FOR A ACTIVE IMPLANTABLE DEVICE

FIELD OF THE INVENTION

The present invention concerns the protection of active implantable devices, particularly pacemakers or cardiac defibrillators. Although in the following description reference is made mainly to the case of a pacemaker, it should be understood that the invention is equally applicable to all types of "Active Implantable Medical Devices," including those devices defined by the 20 Jun. 1990 directive 90/385/EEC, of the European Community Council.

BACKGROUND OF THE INVENTION

Protection of active implantable medical devices is particularly important to provide normal functioning of the implantable device, regardless of the outside environmental conditions, and particularly in the presence of externally originated electromagnetic interference. The various electrodes connected to the implantable device can sense (couple) all sorts of electromagnetic radiation emanating from various external sources. These external sources include engines, televisions, induction plates, portable phones, door locks using R-F tag "keys", anti-theft protection systems, etc. A certain number of medical devices used in the course of surgical interventions also generate electromagnetic radiation, such as electrical R-F surgery devices, cauterization instruments with alternating current, external defibrillators, etc.

Such externally originated electromagnetic radiation can induce or produce parasitic signals in the active implantable medical device which perturb the operation of the device, which perturbations can be very different in nature from the normal signals: prolonged or brief overvoltages (i.e., an excessive signal amplitude), induced currents, radio or high frequency signals of a wide variety of spectral characteristics (in particular, the spectrum spreading typically from one to several megahertz), etc. The different natures of these perturbations render it difficult to provide protection for the pacemaker that is complete and efficient in all circumstances of electromagnetic perturbations.

The externally originated parasitic signals appearing in the active implantable medical device, which are often designated under the term "EMI" (ElectroMagnetic Interference) and hereinafter called "ElectroMagnetic perturbations", or more simply "perturbations", have, for a first effect, to superpose a perturbation on the cardiac signal. This results in a risk of disturbing the functioning of the pacemaker, which would respond to a perturbation treating it as a condition that is in the accepted range of possible conditions, but which does not reflect the actual condition (e.g., treating a perturbation as a natural (sensed) or paced (stimulated) cardiac event). Therefore, the pacemaker should detect perturbations and, if they exceed a given threshold in spite of the protection circuits provided or of circuits inside the pacemaker to suppress perturbations that are coupled into the pacemaker, then the pacemaker should switch into a "perturbation" operating mode, where it will function in an autonomous manner until the level of the coupled perturbation falls under a predetermined threshold.

Another adverse effect of perturbations sensed by the pacemaker is the risk of destruction or damage due to voltages or excessive currents introduced in the pacemaker circuits; it is therefore absolutely indispensable to limit voltages and currents in cardiac probes at the input of the device.

In this regard, very strict standards have been defined in the industry. For example, the standard designated CEN-ELEC EN 50061 Amendment 1 "Security of implantable cardiac pacemakers", defines the levels of required minimal protection as well as a number of test procedures to verify the conformity of pacemakers to the standard.

Up until now, the protection against perturbations of external origin has been realized by the use of Zener diodes, in the form of discrete components mounted on the microchip (i.e., integrated circuit or circuits) of the pacemaker at the input connector where the various probes (leads) are connected to the device. These Zener diodes insure a limit of the overvoltages susceptible to appear at the input of the pacemaker (the voltage limit is the voltage of the Zener diode). The diodes are provided to insure a symmetrical protection so as to avoid in particular the effect of demodulating high frequency perturbations.

A problem with the known protection provided by Zener diodes placed at the input of the pacemaker leads is the disadvantage of an increase in the congestion of the pacemaker circuits, due to the need to provide a relatively high number of such supplementary discrete components (one Zener diode at each in/out connection of the pacemaker, necessitating at least two diodes per lead). This is contrary to the general research goal of increased miniaturization of implantable medical devices, particularly in complex devices such as multiple chamber pacemakers, pacemakers connected to a sensor of enslavement (i.e., a rate response pacemaker that monitors a physiological parameter indicative of cardiac output requirements from which a rate responsive pacing rate can be derived), defibrillators, etc.

Concerning efficiency, protection circuits using Zener diodes insure a satisfactory protection against the high voltages linked, for example, to defibrillation shocks. On the other hand, however, perturbating voltages of lower amplitude can be sensed or demodulated in case of ElectroMagnetic Interference and can cause problems with the low voltage circuits of the pacemaker. Classic Zener diode protection circuits are not as effective against such perturbations. Hence, there is a continuing need for improved protection in this area.

The need for improved protection is particularly apparent in the case where circuits of the pacemaker comprise integrated active components functioning with relatively low nominal control voltages, e.g., the gate voltage of an MOS transistor (MOSFET). Up until now, these components using such low control voltages have not been regularly used in implantable devices, in part because the risk of malfunction due to external perturbations has been so high. This has resulted in depriving the field of the advantages of the most recent semiconductor technologies, particularly the benefits of their very high density of integration and their low power consumption—characteristics which are nevertheless particularly desirable for autonomous implantable devices.

OBJECTS AND SUMMARY OF THE INVENTION

It is, therefore, an object of the present invention to provide an active implantable medical device, particularly a cardiac pacemaker or defibrillator, comprising protection circuits that obtain an immunity against ElectroMagnetic perturbations presenting a very great variety of electrical and spectral characteristics. It is another object to provide protection as required by the industry standards in all circumstances, even the most severe.

Another object of the invention is to allow the realization of such a device according to a technology utilizing nominal control voltages of low value, while obtaining a protection that rigorously conforms to the industry standards.

Another object of the invention is to contribute to the miniaturization of the device, by reducing to a minimum the number of discrete components added to the protection circuits.

Another object of the invention is to propose protection circuits that could be usable and adaptable to various semiconductor integration technologies (for example, partially bipolar technology and partially CMOS, or monolithic BiCMOS technology).

To this end, the invention broadly concerns a structure in which at least the active components of the circuit means for protection against electromagnetic perturbations of external origin are components integrated in a monolithic manner with the microchip (integrated circuit) and comprise input circuits for signals and a switch circuit for the commutation of electrodes. According to a first particular aspect of the invention, the switch circuit comprises static switches with a control voltage significantly greater than the voltage of the power source (i.e., the battery) of the device, and the device delivers logic control signals having a voltage that is lower in magnitude than the switch control voltage, and the circuit means of protection comprises means for translating a voltage to raise, in absolute value, the logic control signal level to a value that is compatible with the static switch control voltages, and that is greater than or equal to the nominal level of parasitic voltages resulting from electromagnetic perturbations which are susceptible to appear on the static switch input. When logic control signals are at a lower level than the nominal level of parasitic voltages, the voltage translating means delivers control voltages at a level that is appreciably greater than or equal to the nominal level of parasitic voltages and are symmetrical, and thus able to avoid essentially the phenomena of demodulation of signals in the case of high alternating frequency (e.g., radiofrequency) perturbations.

Very advantageously, the control voltage levels delivered by the translating means are produced by an integrated monolithic power supply circuit for raising the voltage, this circuit preferably comprising at least one charge pump circuit and/or a voltage doubler circuit and/or a voltage clamping circuit. The bulk substrate of the static switches can be polarized by the same negative power supply voltage which is used in the translator voltage circuit.

According to another aspect of the invention, the circuit means of protection comprise, in addition, a means of "overpowering" comprising a component connected, on the one hand, to an input for an input signal and, on the other hand, to a power line delivering a potential corresponding to the control voltage level produced by the voltage translating circuit means. This component is susceptible to enter a conduction state when the voltage on the corresponding circuit input exceeds, in absolute value, the voltage on the aforementioned power line, in a manner to maintain on the power line a voltage that is always, in absolute value, the highest magnitude in the circuit, even in case of high level perturbations.

According to another aspect of the invention, the circuit means of protection comprise a integrated monolithic voltage limiting circuit connected, on the one hand, to an input for an input signal and, on the other hand, to a ground potential of the device. The voltage limiting circuit can preferably comprise an amplifier circuit of the type "Top to bottom," (as described below) with its conduction current triggered by the voltage.

In an advantageous embodiment of the invention, the circuit means of protection comprise voltage limiting circuits, each comprising, in an integrated and monolithic form, a dipole with a symmetrical structure of "top to bottom" circuits, of which each half comprises a first and a second bipolar transistor connected in series, the emitter of the first transistor being connected to one of the poles of the voltage limiting circuit, the collector of the first transistor being connected to the emitter of the second transistor, the collector of the second transistor being connected to the other pole of the voltage limiting circuit, a resistor being connected between the base and the emitter of the first transistor, and at least two Zener diodes being connected in opposition between the base of the first transistor and the collector of the second transistor.

BRIEF DESCRIPTION OF THE DRAWINGS

Other characteristics and advantages of the invention will appear in the detailed description of a preferred embodiment which follows, made with reference to drawings annexed, in which like reference numerals refer to like elements, and in which.

DETAILED DESCRIPTION OF THE INVENTION

The configuration that is described below corresponds to that of a dual-chamber pacemaker, but this example is not of course in any way restrictive, in that the invention also is applicable to single and multi chamber pacemakers, to pacemakers enslaved or not (therefore comprising one or more supplementary electrodes for measuring a physiological parameter), to the circuits for detection/stimulation of a defibrillator and to active implantable medical devices other than the foregoing cardiac sense/control devices.

Figure 1:
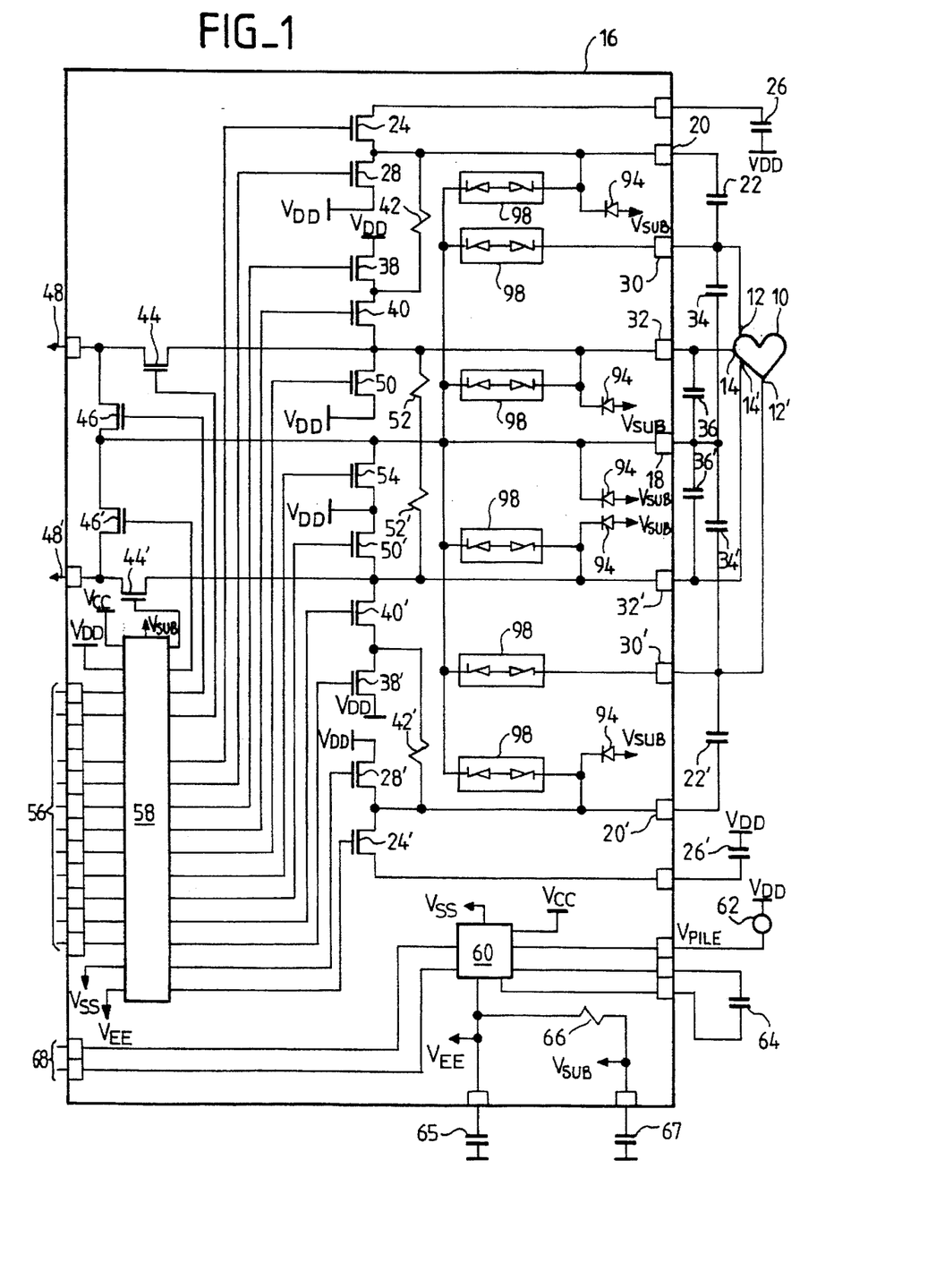
FIG. 1 is a circuit schematic diagram of a microchip in a cardiac pacemaker, which includes power supply, switching and protection circuits, in accordance with a preferred embodiment of the invention.

Referring to FIG. 1, the reference 10 designates a heart on which have been connected various electrodes whose configuration corresponds to that of a dual chamber pacemaker, namely distal atrial electrode 12 and proximal atrial electrode 14, and distal ventricular electrode 12' and proximal ventricular electrode 14'. In the example described, circuits and elements relative to the ventricular detection or stimulation are designated by the same reference numerals used for the atrial detection or stimulation, with the addition of a "prime". These circuits operate in the same manner and hence typically only one explanation is provided.

The different cardiac electrodes are connected, directly or via external capacitors, to a first microchip 16 of the pacemaker through the electrode input/output ports (30, 20, 32, 50', 20', 32'). The case (not shown) of the pacemaker is periodically connected to the ground of the circuit, corresponding to the electrode input port 18, particularly in the case of a unipolar detection and stimulation.

The cardiac electrodes and the case have several electrical states, including detection or stimulation, and a unipolar or bipolar mode. This implies that the realization of the periodic switching is controlled according to a particular sequence. More precisely, the atrial electrode 12 is connected to an input 20 via a stimulation capacitor 22, the input 20 being able to be commuted by a switch 24 to an external capacitor 26 whose other input is connected to the ground potential (designated VDD on the diagram, and corresponding to the positive input of the battery), or connected directly to VDD by another switch 28. Atrial electrodes 12 and 14 are also connected to connectors 30 and 32 which provide for a bipolar detection (by measure of a differential voltage) of the cardiac activity. These connections are decoupled by respective external capacitors 34 and 36, insuring the filtering of high frequency (greater than 1 Mhz) perturbations. Switches 38 and 40 switch an input resistance 42 out of the circuit (during the stimulation) or in the circuit (at times other than during stimulation) for passing to ground any residual charges subsisting after delivery of a stimulation to the heart-electrode interface. The switch 44 is conductive (passing) in case of bipolar detection, and nonconductive (blocking) in case of unipolar detection, and the switch 46 has the inverse functioning. The detected signal is then directed via lines 48 to the detection differential amplifier (not represented).

The microchip 16 also comprises a switch 50 for the placement in circuit of the atrial ground (in the case of a stimulation); in the absence of commutation, the corresponding electrode (input 32) is connected to ground by the intermediary of a resistor 52 of approximately ten Megaohms (M$\Omega$) allowing to maintain on this input 32 a null (zero) static potential.

The ventricular stimulation circuit is the same as the one previously described, with elements 20' to 52' being identical to elements 20 to 52 as already described.

The circuit also comprises a switch 54 destined for the placement in circuit that selectively connects the case (input 18) to ground. These various switches can be configured to allow operation of all stimulation and detection configurations, including unipolar and bipolar modes. These switches are preferably transistors, such as MOS transistors or equivalent structures.

In the case of an enslaved pacemaker (i.e., a rate responsive pacemaker), it also can include one or several supplementary switches. For example, in the case of a pacemaker enslaved to the respiratory activity, additional switches would be provided to insure the discharge of the capacitance of the injection current commonly used to measure transthoracic impedance variations from which the respiration rate and/or minute volume measures can be derived. Other switching circuits can be anticipated, for example, in the case of an implantable defibrillator.

The role and the operative mode of these different commutations (switching functions) are in themselves well known, and for this reason will not be described more in detail.

The microchip 16 shown in FIG. 1, a microchip in which the components are integrated in a monolithic manner, is associated (i.e., operatively connected) to a second microchip (not represented), which also is integrated in a monolithic manner. The microchip thus includes conventional input/output ports for communication with the second microchip. The second microchip typically comprises a logic control circuit, for example, a microprocessor or an appropriate logic control (solid state machine or hybrid digital and analog control) circuit, in themselves well known and which are not strictly a part of the present invention. This logic control circuit delivers, in particular, the logic control signals 56 to control the various switches in microchip 16, and clock signals 68, which are used by the microchip 16. In accordance with one embodiment of the invention, one controls the different switches using non symmetrical low level logic signals (that is to say a level that is not greater than the voltage level of the battery), and by producing a Gate voltage presenting a "gap" between the control voltages corresponding to the passing state "ON" and the blocking state "OFF". The term "voltage excursion" is hereinafter defined as (1) much greater, in absolute value, than the logic control signal values, and (2) essentially symmetrical in relation to the ground (zero) potential, that is to say the rest potential of all inputs and outputs of the pacemaker (potential VDD=0 V). Possible interference superposing on this rest potential, a large voltage excursion allows to avoid untimely commutation risks, and the symmetrical voltage range in relation to the rest potential avoids all risk linked to a demodulation signal in the case of a high alternating perturbation frequency.

In the illustrated example, switches are N type MOS transistors whose gate is controlled by a voltage presenting the particular voltage excursion indicated above (VCC, VSUB), and whose substrate is connected to a significantly negative power supply voltage (VSUB). To be able to control the transistor gates in these voltage ranges, switches are associated to the voltage translator circuit 58 (also referred to as a "level-shifter") interposed between the nonsymmetrical and low level control signals applied in 56 and the gates of corresponding switches. The voltage translation, explained in more detail below, receive various supply voltages VDD, VSS, VCC, VSUB, and VEE produced by a power supply block 60, the structure of which is represented in detail in FIG. 3.

Power supply block 60 is preferably entirely integrated in monolithic form (as are all the other elements of the microchip 16), and is connected to the negative terminal of a battery 62. The positive battery terminal constitutes the reference potential zero (VDD), i.e., the ground return. Connected to the integrated block 60 are external components capacitor 64 and decoupling capacitors of 65 and 67, whose roles will be explained below. It is noted that microchip 16 also has connected to it a few external capacitors.

Figure 2:
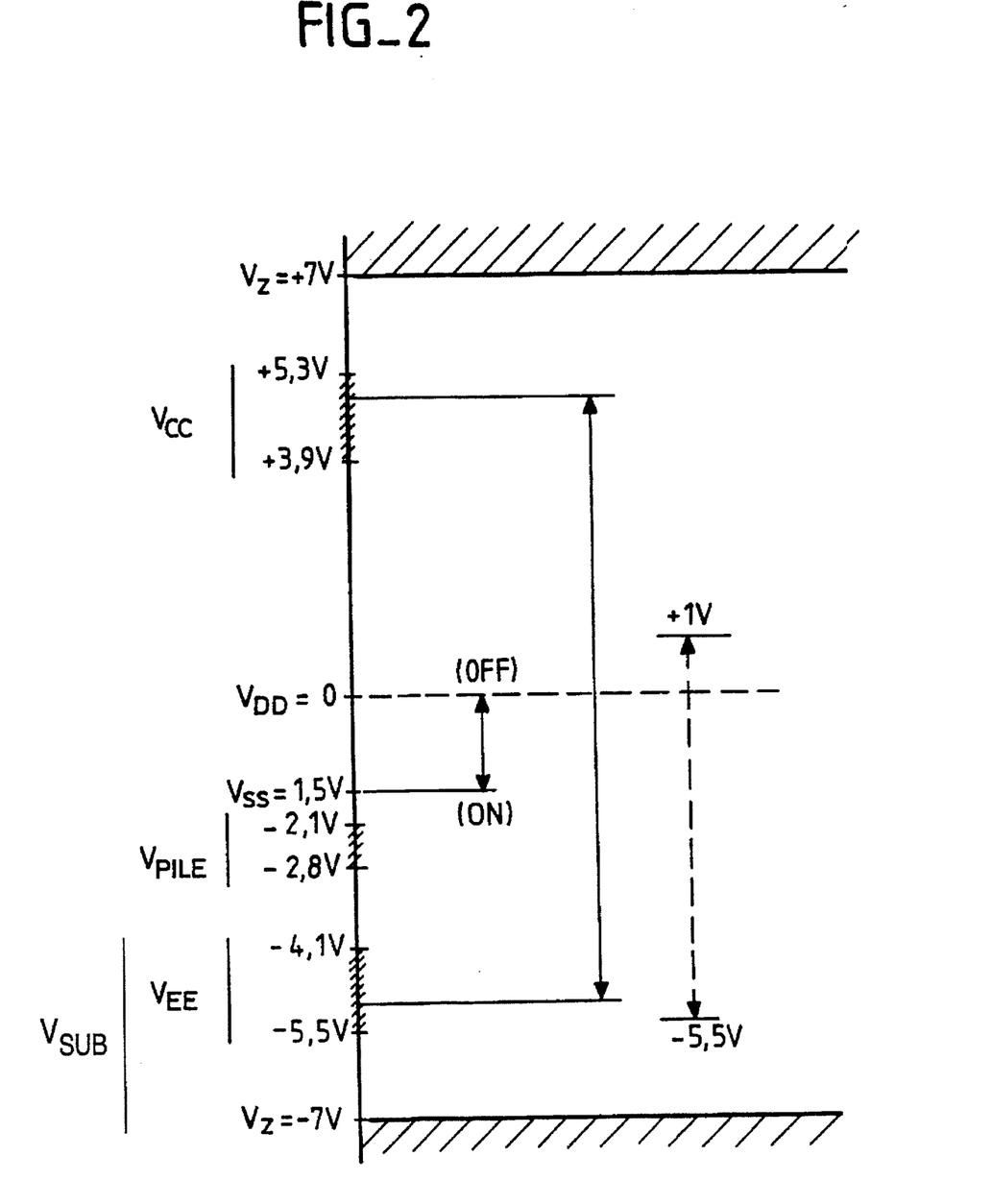
FIG. 2 is a diagram showing the different voltages produced in the circuit of the FIG. 1, and the levels between which these voltages vary.

The various potentials used by the exemplary pacemaker of the invention, and particularly circuits that are to be described, are as follows (with reference to FIG. 2, which represents on a diagram these different potentials, in a manner to show their relative magnitude and their symmetrical or nonsymmetrical character):

VDD: positive terminal of the battery 62, corresponds to the ground reference potential zero.

VPILE: negative terminal of the battery 62 typically at −2.8 V at the beginning of the battery life to −2.1 V at the end of the battery life.

VSS: a regulated negative voltage of −1.5 V±50 mV, used specifically for logic control signals.

VEE: negative voltage, typically comprised between −5.5 V (beginning of life) and −4.1 V (end of life), produced by the block 60 from VDD and VPILE (with a decoupling capacitor 65).

VCC: positive voltage, typically +5.3 V (beginning of life) to +3.9 V (end of life), produced by the block 60 from VDD and VEE (one will note that voltage VCC presents an approximately symmetrical value of the negative voltage VEE produced by the block 60)

VSUB: negative power supply connected to the polarization of the substrates, e.g., p-substrate of microchip 16, (this voltage is a voltage derived from VEE (with a decoupling capacitor 67) by the intermediary of a series limiting resistor (component 66 on FIG. 1, typically an integrated resistance of 300 kΩ)); VSUB is therefore typically between −5.5 V and −4.1 V. More particularly, the resistor 66 has for an object, on the one hand, to limit the current in the leads in the case of a defect and, on the other hand, to protect VEE in the presence of a substrate current induced by an external perturbation (for example, the low current that can appear during a period of voltage limitation).

Figure 3:
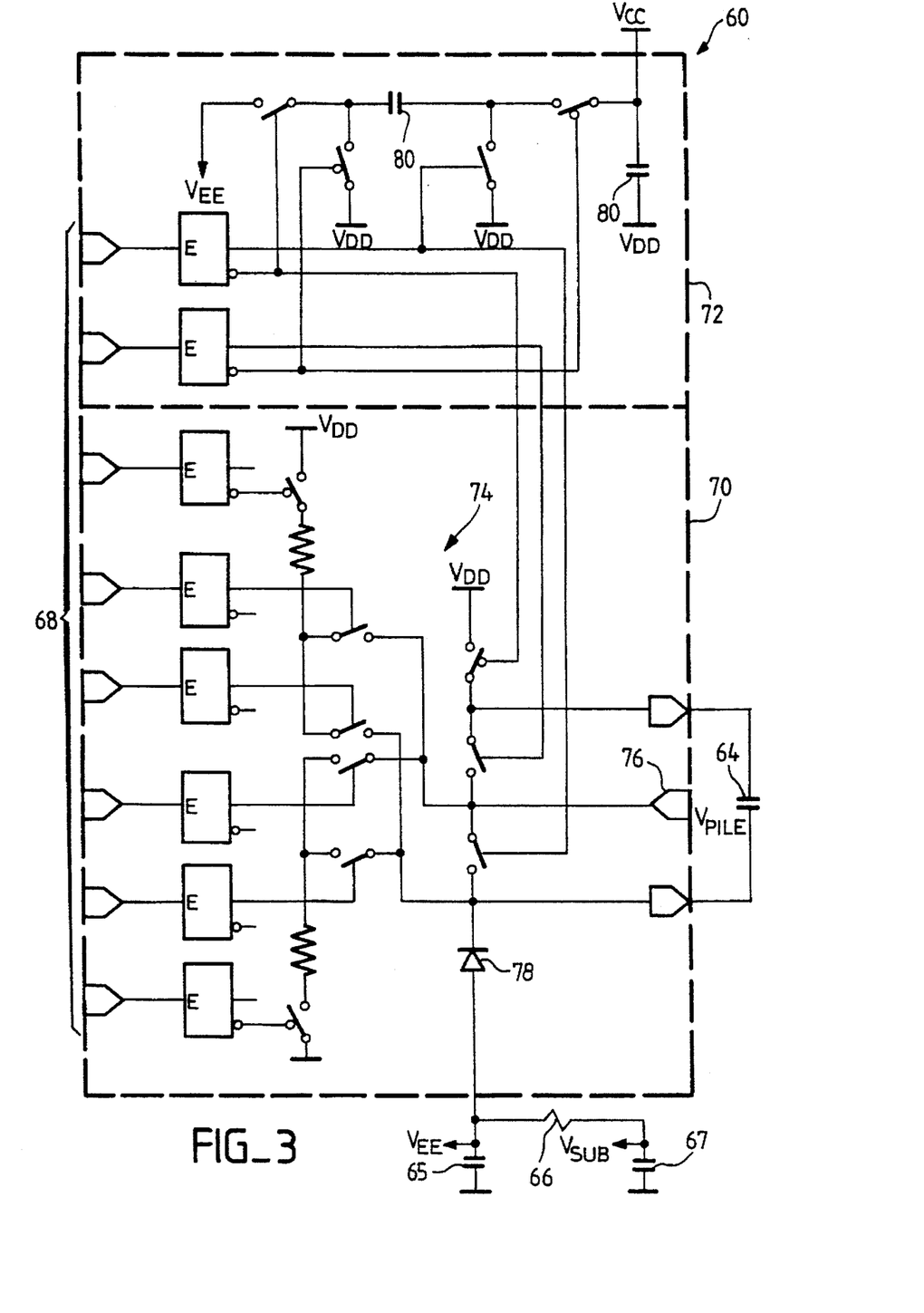
FIG. 3 is a schematic diagram of the power supply circuit of FIG. 1.

With reference to FIG. 3, appreciably symmetrical voltages VCC and VEE/VSUB are produced in the following manner. Block 60 receives clock control signals at input 68 from a logic circuit of the pacemaker (e.g., the second microchip, not shown). Block 60 comprises essentially two subcircuits, namely a subcircuit 70 producing the negative voltages VEE (and therefore VSUB that is directly derived from VEE) from VPILE, and a subcircuit 72 producing the positive voltages VCC from the voltage VEE produced by the subcircuit 70.

The subcircuit 70 is essentially a voltage doubler circuit 74, a structure well known and represented on FIG. 3 (and which needs not be described in more detail for this reason). This "doubling circuit" is performed by a plurality of translation sequences in an appropriate manner by logic signals 68, associated switches, and the external capacitor 64. It operates to transform the voltage battery VPILE comprised between −2.8 V and −2.1 V, to a voltage VEE (and therefore a voltage VSUB) comprised between −5.5 V and −4.1 V. The obtained voltage is delivered via a diode 78 to low threshold voltage, polarized by a current that is applied from an external source (not represented) so as to limit to the maximum voltage drop to the level of this component.

The subcircuit 72 produces the voltage from VEE a positive voltage VCC, comprised between +5.3 V and +3.9 V, for example, by means a circuit of the charge pump type comprising a plurality of switches sequenced by clock signals 68 and integrated capacitor 80, according to a known scheme, which needs not be described more in detail for this reason.

A charge pump circuit is advantageous because, it can be realized entirely integrated; others implementations are however possible, for example, in voltage clamping circuits. In the latter case, it may be necessary to anticipate so many switching circuits that it also is necessary to provide refresh signals for switches whose passing state has to be maintained during the duration of a cycle. In view of the production of these various voltages, it is possible, by applying logic control signals 56 (FIG. 1) ranging between VDD and VSS (0 V and −1.5 V), to produce on gates of switches control voltages whose voltage excursion is comprised between VEE and VCC, that is typically between −5.5 V and +5.3 V in beginning of the battery life and between −4.1 V to +3.9 V at the end of the battery life), therefore with voltages that are much greater, by both about three times in absolute magnitude, and symmetrical, insuring therefore, enhanced immunity to external perturbations which otherwise would be susceptible to influence the control of the switches.

The voltage translator circuit 58 (FIG. 1), includes a plurality of well-known circuits that are connected to the various potential VCC, VDD, VSS, VEE respectively, interposed on each line of transmission of the logic control signal to insure the amplification and the symmetry of the control voltage VDD/VSS to VCC/VEE, and therefore the amplification and the symmetry of the dynamic control of the switches. These voltage translator circuits can be advantageously realized in an entirely integrated monolithic form in the microchip 16, therefore with possibility of a great density of integration and, consequently, an enhanced extreme miniaturization.

In accordance with this circuit configuration, one is assured that the control of the various switches of the circuit 16 will be protected from electromagnetic perturbations that, otherwise, would have been able to drive the switches in some conditions, with a result of unpredictable and erroneous commutations of the switches.

In addition, to maintain all the time, and in spite of all perturbations that might occur, a voltage VSUB that is the most negative voltage of the circuit, it is expected to provide the circuit a dynamic power supply, such that even the strongly negative perturbations will not disturb the relative gaps between the various voltage levels produced by the voltage translations and applied to the various switches, and thus avoid adverse influences on the functioning of the circuit.

Figure 4:
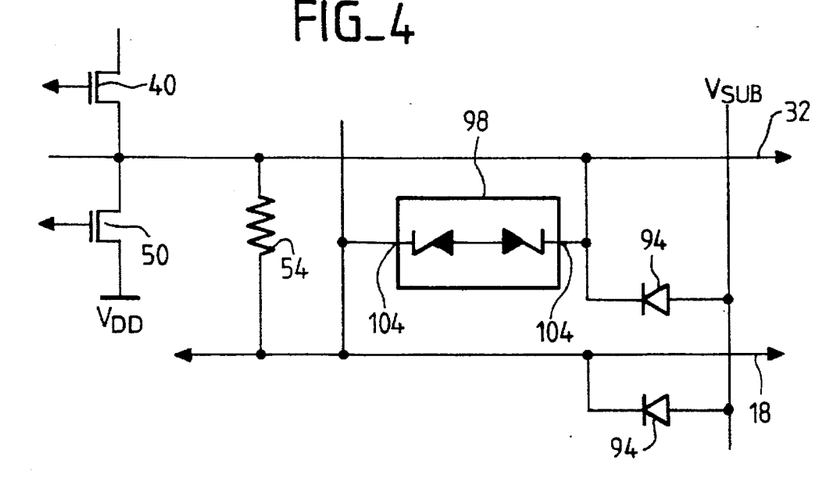
FIG. 4 is an enlarged schematic circuit diagram of a part of the circuit of FIG. 1, showing a dynamic polarization and protection against overvoltages.

To this end, each of connectors 20, 20', 32, 32' and 18 is connected, on the one hand, to the cathode of a diode 94 whose anode is connected to VSUB (the diodes 94 are also shown in FIG. 4). Concerning the atrial and ventricular ground polarization, resistors 52 and 52', which connect connectors 32 and 32' to the case (input 18), allow to avoid all possible leakage current. When one of connectors 20, 20', 32, 32' and 18 has, due to the presence of a parasite, a potential more negative than VSUB, the diodes become conducting. This allows the "overpowering" of the assembly from the points connected to VSUB, and thus avoid all risk of untimely commutation due to the presence of the perturbation. Concerning the protection against large overvoltages, the protection is conventionally realized, in known pacemakers, by use of Zener diodes connected in opposition between each input connection and ground. These diodes insure a symmetrical voltage limitation for voltages greater than the Zener voltage, typically of voltages greater in absolute value to ±7 V (see the cross-hatched upper and lower bounds in FIG. 2).

Figure 5:
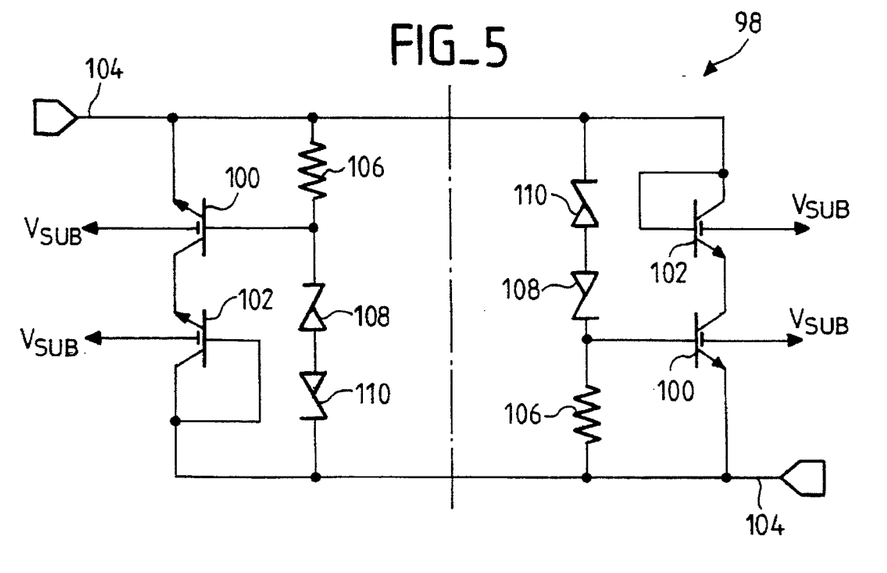
FIG. 5 is a schematic circuit diagram of the protection circuit against overvoltages of the circuits of FIGS. 1 and 4.

The present invention proposes to replace these Zener components, that were up till now discrete components carried on the circuit, by entirely integrated monolithic protection circuits. These protection circuits, according to the invention, are dipoles connected in the same manner as the Zener diodes in opposition as in the prior art. They are susceptible to drive comparable current levels (several hundred of milliamperes), despite an entirely integrated structure, and result in much lower congestion of circuit components. These circuits of voltage limitation 98 are equal in number to the number of connectors 20, 20', 30, 30', 32, 32' and are connected between each respective input and the ground of the case, corresponding to the input 18. To allow their integration, these circuits 98 each have, in a preferred embodiment, the "top to bottom" structure illustrated in FIG. 5, that is a symmetrical structure each of whose halves comprises two bipolar transistors 100, 102 connected in series, the emitter of the transistor 100 being connected to one of poles 104 of the circuit 98, the collector of this transistor 100 being connected to the emitter of the transistor 102, and the collector of the transistor 102 being connected to the other pole 104 of the circuit 98. Between the base and emitter of the transistor 100 is connected a resistor 106. Between the base of the transistor 100 and the collector of the transistor 102 are connected in opposition two (or more) integrated Zener diodes 108, 110, allowing to define the voltage limitation. The dipole thus operates in conduction when the difference of potential across the poles 104 exceeds, in absolute value, 7 V. It thus functions as a current amplifier triggered by the voltage differences to conduct to limit the voltage, and can drive between its poles 104 currents up to 300 mA. It also can absorb current peaks of 3A having a pulse width of 10 ms. It is therefore able to support, without risk of destruction, perturbations even of very strong energy.

One skilled in the art will appreciate that the present invention can be practiced by other than the described embodiments, which are presented for purposes of illustration and not limitation.

We claim:

1. An active implantable medical device comprising:
   a battery having a first voltage;
   a microchip circuit having an electrode input port and a circuit element;
   a power supply circuit, coupled to the battery first voltage, having a second voltage output and a third voltage output, the second and third voltages being greater than the first voltage;
   a switch connected between said electrode input port and said circuit element having a first state and a second state to switch selectively the electrode input to the circuit element and a control input to select the switch state in response to the second and third voltages; and
   a protection circuit connected to said electrode input port including at least one active component, the active component having a state that is responsive to an externally originated perturbation including a normal operating state in an absence of said perturbation and a protective operating state in the presence of said perturbation, wherein the protective operating state couples one of said second and third voltages to said switch control input and wherein the protection circuit, switch, power supply circuit and microchip further comprise a monolithically integrated circuit.

2. The device of claim 1, further comprising:
   a control circuit having a plurality of logic control voltage output signals, each logic control voltage signal having one of a first voltage value and a second voltage value (VDD, VSS), said plurality logic control voltage signals being connected to said microchip;
   wherein the microchip further comprises a logic control signal input port to receive the plurality of logic control voltage output signals;
   wherein the electrode input port further comprises a first plurality of electrode input ports and the circuit element further comprises a second plurality of elements selected from among the group consisting of resistors, capacitors, the first voltage value, the second voltage value and an output port;
   wherein the switch further comprises a third plurality of static switches, each static switch having a first state and a second state and a control input to receive a control voltage and a switch control level to select the switch state in response to the input control voltage being greater or less than the switch control level, each static switch being coupled to one of said first plurality of electrode input ports to switch selectively said one electrode input port to one of said second plurality of elements;
   wherein said power supply circuit further comprises a control voltage (VSUB, VCC) greater than the battery first voltage; and
   wherein the protection circuit further comprises:
   a voltage translator circuit having a plurality of outputs, said plurality of outputs being connected to the control inputs of said third plurality of static switches, and said voltage translator circuit being coupled to said control voltage (VCC, VSUB) and said logic
   control voltage signal first and second voltage values (VDD, VSS) for providing a selected voltage output level at each one of said plurality of voltage translator circuit outputs that is greater in absolute value than the logic control voltage signals first and second voltage values (VDD, VSS) and compatible with the switch control level, and a voltage level that is greater than or equal to a nominal level of parasitic voltages resulting from said perturbations at said electrode input port.

3. The device of claim 2, in which logic control voltage signals are less than the nominal level of parasitic voltages, and the voltage translator circuit plurality of output control voltages responsive to said logic control voltage output signals are appreciably greater than or equal to the nominal level of parasitic voltages and symmetrical, thereby to minimize demodulation of a perturbation corresponding to a high frequency signal.

4. The device of claim 2, wherein, the power supply circuit further comprises a plurality of reference potential output levels, wherein the voltage translator circuit selected voltage output level is produced by the power supply circuit, and wherein the voltage translator circuit is integrated in the monolithically integrated circuit.

5. The device of claim 4, in which the integrated monolithic voltage translator circuit and power supply circuits comprise at least one of a charge pump circuit, a voltage doubling circuit, and a voltage clamping circuit, each circuit having an output, and the voltage translator circuit is responsive to said output to produce said voltage output level.

6. The device of claim 4, wherein the voltage translator circuit has a negative power supply (VSUB) and each of the static switches further comprises a bulk substrate connected to the negative power supply (VSUB).

7. The device of claim 2, wherein the monolithically integrated protection circuit further comprises a plurality of voltage limiting circuits (98) and a pair of poles, each voltage limiting circuit being connected between said pair of poles (104) and comprising a dipole having a symmetrical structure having a first half and a second half, each half comprising a first bipolar transistor (100) and a second (102) bipolar transistor connected in series, the first transistor having an emitter connected to one of said poles (104), the first transistor having a collector connected to an emitter of the second transistor, the second transistor having a collector connected to the other pole (104), a resistor (106) connected between a base and the emitter of the first transistor, and at least two Zener diodes (108, 110) connected in opposition between a base of the first transistor and the collector of the second transistor.

8. The device of claim 1, wherein the protection circuit further comprises a component having a conduction state connected between an electrode input port and a potential corresponding to a predetermined voltage amplitude, said component being susceptible to enter the conduction state when the voltage on the electrode input port exceeds, in absolute value, said potential.

9. The device of claim 8 further comprising a maximal voltage value, wherein, in response to a large perturbation, the protection circuit operates to maintain the potential at a voltage that is, in absolute value, at the maximal value.

10. The device of claim 1, wherein said microchip further comprises a ground potential and the integrated monolithic circuit of the protection circuit further comprises a voltage limiting circuit (98) connected to the electrode input port and said ground potential.

11. The device of the claim 10, wherein said monolithic circuit further comprises a pair of poles and the voltage limiting circuit further comprises a current amplifier, the amplifier being operable to transfer current between said pair of poles in response to a voltage corresponding to a predetermined threshold.

12. The device of claim 11 wherein the current amplifier is inserted between said pair of poles and further comprises a dipole having a symmetrical structure having a first half and a second half, each half comprising a first bipolar transistor (100) and a second (102) bipolar transistor connected in series, the first transistor having an emitter connected to one of said poles (104), the first transistor having a collector connected to an emitter of the second transistor, the second transistor having a collector connected to the other pole (104), a resistor (106) connected between a base and the emitter of the first transistor, and at least two Zener diodes (108, 110) connected in opposition between a base of the first transistor and the collector of the second transistor.

* * * * *

UNITED STATES PATENT AND TRADEMARK OFFICE
CERTIFICATE OF CORRECTION

PATENT NO. : 5,649,965
DATED : July 22, 1997
INVENTOR(S) : Pons et al.

It is certified that error appears in the above-identified patent and that said Letters Patent is hereby corrected as shown below:

Column 7, line 47, after "example" delete "in";

column 9, line 26, after "input", insert --port--

Signed and Sealed this

Second Day of February, 1999

Attest:

Attesting Officer

Acting Commissioner of Patents and Trademarks